(12) United States Patent
Wallace

(10) Patent No.: US 7,024,945 B2
(45) Date of Patent: *Apr. 11, 2006

(54) FLOW SENSING APPARATUS

(75) Inventor: Allan Wallace, Tranmere (AU)

(73) Assignee: Compumedics Limited, Abbotsford (AU)

( * ) Notice: Subject to any disclaimer, the term of this patent is extended or adjusted under 35 U.S.C. 154(b) by 144 days.

This patent is subject to a terminal disclaimer.

(21) Appl. No.: 10/080,744

(22) Filed: Feb. 22, 2002

(65) Prior Publication Data

US 2003/0159697 A1     Aug. 28, 2003

(51) Int. Cl.
  *G01F 1/74* (2006.01)
(52) U.S. Cl. .................................. 73/861.74
(58) Field of Classification Search ............ 73/861.74, 73/861.71, 861.24, 861.77, 861.355, 861.08, 73/861.75, 861.79, 861.81, 861.83; 128/204.23, 128/205.23
  See application file for complete search history.

(56) References Cited

U.S. PATENT DOCUMENTS

| | | | | |
|---|---|---|---|---|
| 3,636,767 A * | 1/1972 | Duffy | ...................... | 73/861.77 |
| 4,141,355 A | 2/1979 | Apple | ...................... | 128/145.6 |
| 4,173,975 A | 11/1979 | DeLong et al. | ......... | 128/142 R |
| 4,181,020 A * | 1/1980 | Herzl | ....................... | 73/861.24 |
| 4,307,619 A * | 12/1981 | Herzl | ....................... | 73/861.24 |
| 4,397,195 A | 8/1983 | Hayward | ................. | 73/861.74 |
| 4,428,242 A * | 1/1984 | Holstrom | ................ | 73/861.75 |
| 4,509,551 A | 4/1985 | Luper | ...................... | 137/554 |
| 4,546,793 A | 10/1985 | Stupecky | .................... | 137/554 |
| 4,557,674 A | 12/1985 | Arnett, Jr. | ..................... | 418/15 |
| 4,726,366 A | 2/1988 | Apple et al. | ............ | 128/204.21 |
| 4,745,925 A | 5/1988 | Dietz | ......................... | 128/725 |
| 4,773,375 A | 9/1988 | Okino et al. | ................. | 123/488 |
| 4,777,833 A * | 10/1988 | Carpenter | .............. | 73/861.355 |
| 4,790,195 A | 12/1988 | Feller | ....................... | 73/861.77 |
| 4,860,764 A | 8/1989 | Hudimac, Jr. | ............... | 128/725 |
| 4,860,765 A | 8/1989 | Hudimac, Jr. | ............... | 128/725 |
| 4,862,898 A | 9/1989 | Hudimac, Jr. | ............... | 128/725 |
| 4,957,107 A | 9/1990 | Sipin | ..................... | 128/204.21 |
| 5,021,619 A * | 6/1991 | Hutchinson | ........... | 200/81.9 M |
| 5,182,952 A * | 2/1993 | Pyzik | ....................... | 73/861.79 |
| 5,195,845 A | 3/1993 | Parks | ......................... | 405/74 |
| 5,259,373 A * | 11/1993 | Gruenke et al. | ........ | 128/204.23 |
| 5,372,544 A | 12/1994 | Gervais | ...................... | 454/256 |
| 5,469,750 A | 11/1995 | Lloyd | ....................... | 73/861.61 |
| 5,557,185 A | 9/1996 | Jacobsen | ............... | 318/568.16 |
| 5,558,086 A | 9/1996 | Smith | .................... | 128/204.26 |
| 5,663,508 A * | 9/1997 | Sparks | .................... | 73/861.71 |
| 5,685,697 A | 11/1997 | Buchanan, Jr. et al. | ....... | 417/12 |
| 5,767,419 A * | 6/1998 | Hutchinson | .............. | 73/861.74 |
| 5,895,866 A * | 4/1999 | Neukermans et al. | .... | 73/861.74 |
| 5,913,307 A * | 6/1999 | Taieb et al. | ............ | 128/205.23 |
| 5,945,608 A * | 8/1999 | Hutchinson | .............. | 73/861.24 |
| 6,119,686 A | 9/2000 | Somerson et al. | ..... | 128/202.22 |
| 6,119,723 A | 9/2000 | Kenyon | ....................... | 137/527 |
| 6,129,113 A | 10/2000 | Van Becelaere | ............ | 137/557 |
| 6,212,958 B1 * | 4/2001 | Conley | .................... | 73/861.74 |
| 6,557,574 B1 * | 5/2003 | Federspiel | .................. | 137/12 |
| 6,681,645 B1 * | 1/2004 | Feller | ....................... | 73/861.71 |

* cited by examiner

*Primary Examiner*—Edward Lefkowitz
*Assistant Examiner*—Jewel V. Thompson
(74) *Attorney, Agent, or Firm*—Fulbright & Jaworski L.L.P.

(57) ABSTRACT

A flow sensing apparatus for detecting fluid flow rate and direction is described. The flow sensing apparatus includes a flow-responsive element projecting into the fluid flow path, and a position sensor which detects the degree and direction of any change in position of the flow responsive element in response to the fluid flow.

8 Claims, 14 Drawing Sheets

FLOW SENSING APPARATUS

FIELD

This invention relates to a fluid flow sensing apparatus which has a high sensitivity at low fluid flow rates. The flow sensing apparatus is particularly suitable for sensing respiration and is useful for treating respiratory sleep disorders.

BACKGROUND

The study and treatment of respiratory sleep disorders, such as sleep apnea, has resulted in the development of numerous diagnostic, monitoring and treatment devices. One type of these devices is the Positive Air Pressure ("PAP") device, in which the patient receives a controlled amount of gas depending on a variety of factors. For example, in a Bi-Positive Air Pressure ("Bi-PAP") device, the patient receives gas at one pressure during inhaling, and at another pressure while exhaling. PAP devices are primarily used for treatment of respiratory sleep disorders, but can be used for diagnostic and monitoring functions as well.

Devices such as the Bi-PAP device must, therefore, have the ability to quickly determine the patient's respiratory state and apply the correct gas pressure associated therewith.

Previous attempts to provide this ability in positive air pressure devices have involved the use of "on-off" switches or valves as flow sensors. Other methods include the use of pressure transducers, which can be cumbersome and are generally not cost effective.

One problem associated with the switches or valves is that they cannot provide an analog signal indicative of the patient's breathing force. Another problem with existing flow sensors is that at low fluid flow rates or pressures, the sensor sensitivity is low, and the sensitivity only improves as the flow increases. For the treatment of sleep disorders such as sleep apnea, it is especially important for these devices to be able to detect and respond to very low fluid flow rates.

There is a need for a flow sensing device which can generate an analog signal in response to a patient's breathing, has a high sensitivity at a low fluid flow pressure, and is economical and compact so as to be suitable for use with a variety of positive air pressure devices.

SUMMARY OF THE INVENTION

The present invention is directed to a fluid flow sensing apparatus comprising a flow-responsive element projecting into a fluid flow path and a position sensor in communication with the element to detect a change in position of the element in response to a fluid flow. The apparatus has a sensitivity that is generally inversely related to a pressure generated by the fluid flow. In one embodiment, when the fluid is a gas or a combination of gases, the apparatus has a sensitivity that is inversely related to the pressure generated by the gas when the gas flow rate is greater than about 20 liters/minute (hereinafter, "l/min"). The flow-responsive element can respond to fluid in flow in more than one direction, and preferably responds when the fluid flow rate is between about −10 l/min to about 150 l/min for gaseous fluids. The fluid flow sensing apparatus can also be used to detect flow rates of other fluids, such as liquids. The position sensor may also be in communication with a fluid flow controller to control the fluid flow in response to the change in position information detected by the sensor.

The present invention is also directed to a device for delivering gas to a patient, comprising a gas flow generator to generate a positive gas pressure along a gas flow path, a multidirectional gas flow sensing apparatus to detect a patient breathing, a gas flow controller to control the gas pressure in response to the patient breathing, and a patient breath interface to monitor the patient's breathing, wherein the gas flow sensing apparatus comprises a flow-responsive element projecting into the gas flow path and a position sensor in communication with the element to detect a change in position of the element in response to the patient breathing. The position sensor is also in communication with the gas flow controller to control the gas pressure based on the change in position information provided by the position sensor.

The position sensor has a sensitivity that is inversely related to a fluid dynamic pressure generated by the patient breathing. The flow-responsive element responds to one degree when the patient is inhaling and to another degree when the patient is exhaling. The gas flow generator generates a gas pressure for inhaling and a different gas pressure for exhaling in response to the change in position of the element, and such change in position is proportional to a force generated by the patient breathing. The flow-responsive element can be made from a variety of materials such as plastic, metal, ceramics, paper, composite materials, and the like.

In one embodiment, the position sensor preferably comprises one or more magnets and a Hall Effect sensor. The magnet is preferably attached to the flow-responsive element at a location on the element that is out of the gas flow path. The Hall Effect sensor is preferably positioned proximate to the magnet and spaced apart from the flow-responsive element. Preferably, there are a plurality of magnets, with each magnet being positioned on an opposite surface of the flow-responsive element and attached to the element by attractive magnetic forces. In one embodiment, the gas flow generator is a dual pressure blower. Preferably, the gas flow controller is a valve.

DESCRIPTION OF THE DRAWINGS

FIG. 3b is a perspective view of another embodiment of the flow sensor of the present invention which includes the deformable element shown in FIG. 3a.

DETAILED DESCRIPTION

Figure 1:
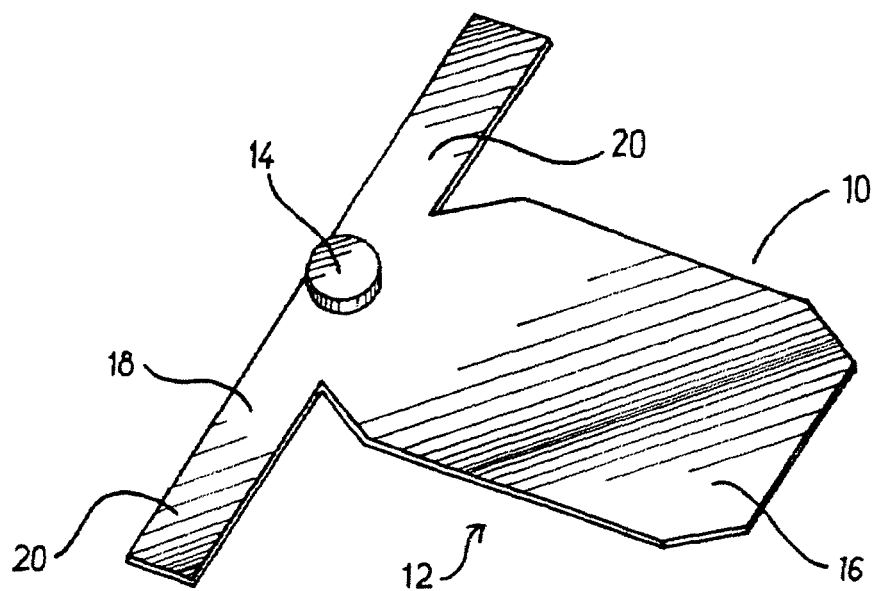
FIG. 1 is a perspective view of one embodiment of the flow sensor of the present invention.

FIG. 1 shows one embodiment of a flow sensor 10 in accordance with the present invention. Flow sensor 10 includes flow-responsive element 12 and position sensor 14. In the embodiment shown in FIG. 1, flow-responsive element 12 includes a paddle portion 16 and a torsion strip portion 18 to which sensor 14 is attached. Preferably, there are two position sensors 14 (the second sensor is not shown in FIG. 1), one attached to each planar surface of the torsion strip portion 18.

In operation, the ends 20 of torsion strip portion 18 are held in a fixed position, with paddle portion 16 positioned in the fluid flow path approximately normal to the fluid flow. When there is no fluid flow in the flow path, paddle portion 16 is said to be in the "zero-flow" position. As fluid flows along the flow path the fluid dynamic pressure generated by the fluid flow operates against the paddle portion 16. Paddle portion 16 changes position in response to the pressure. In turn, torsion strip portion 18 deforms in response to the torque applied by the change in position of paddle portion 16. The position sensors 14 sense the deformation of the torsion strip portion 18 and can transmit a signal to a fluid flow controller that corresponds to the degree of change in position of flow-responsive element 12. The controller can adjust the flow based on the signal from position sensors 14.

Flow-responsive element 12 is preferably subjected to biasing forces which bias element 12 into the zero-flow position, so that as the fluid flow changes, the response of element 12 changes, and when there is no fluid flow, element 12 is biased into the zero-flow position. Such forces may include torsional forces from a torsion coil spring, gravitational forces, or material structural biasing forces in the material used to make element 12 to bias element 12 into the zero-flow position.

The change in position of flow-responsive element 12 relative the zero-flow position is indicative of the patient's breathing direction and strength. Flow-responsive element 12 will preferably change position along a continuum, and the degrees of change in position, in other words, the sensitivity of the flow sensing apparatus, can be controlled by the selection of material or materials used to make element 12 and by the selection of the biasing force.

Flow-responsive element 12 can be made of a wide variety of materials including: plastics; metal, such as brass, aluminum or steel; composite materials, such as fiber reinforced plastics; ceramics, such as glass; paper; or any combination of materials which provide the desired properties.

Preferably, the material used for flow-responsive element 12 is mechanically stable with little or no creep, has a low elastic modulus so it changes position easily, is relatively impervious to normal temperature or humid variations, has good internal damping to reduce the tendency to flutter, is consistently easy to manufacture and can be produced at a low cost.

Figure 2:
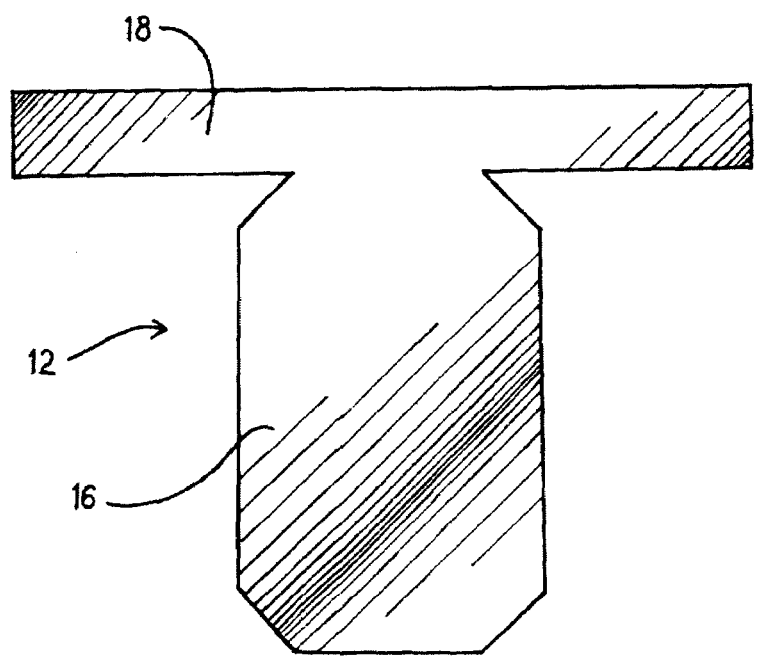
FIG. 2 is a plan view of one embodiment of the deformable element of the present invention.

One particularly preferred material for flow-responsive element 12 is Mylar®, a plastic film composed of the polyester polyethylene terephthalate, available from DuPont. Other plastic films or similar materials may also be used. As shown in FIG. 2, the paddle portion 16 and torsion strip 18 of flow-responsive element 12 can be made from a single piece of material. Alternatively, paddle portion 16 and torsion strip 18 can be made of different materials. Preferably, paddle portion 16 is made of a relatively rigid material and torsion strip portion 18 is made of a relatively elastic material to maximize the twisting motion sensed by position sensors 14 when dynamic pressure is applied to paddle portion 16.

Figure 3A:
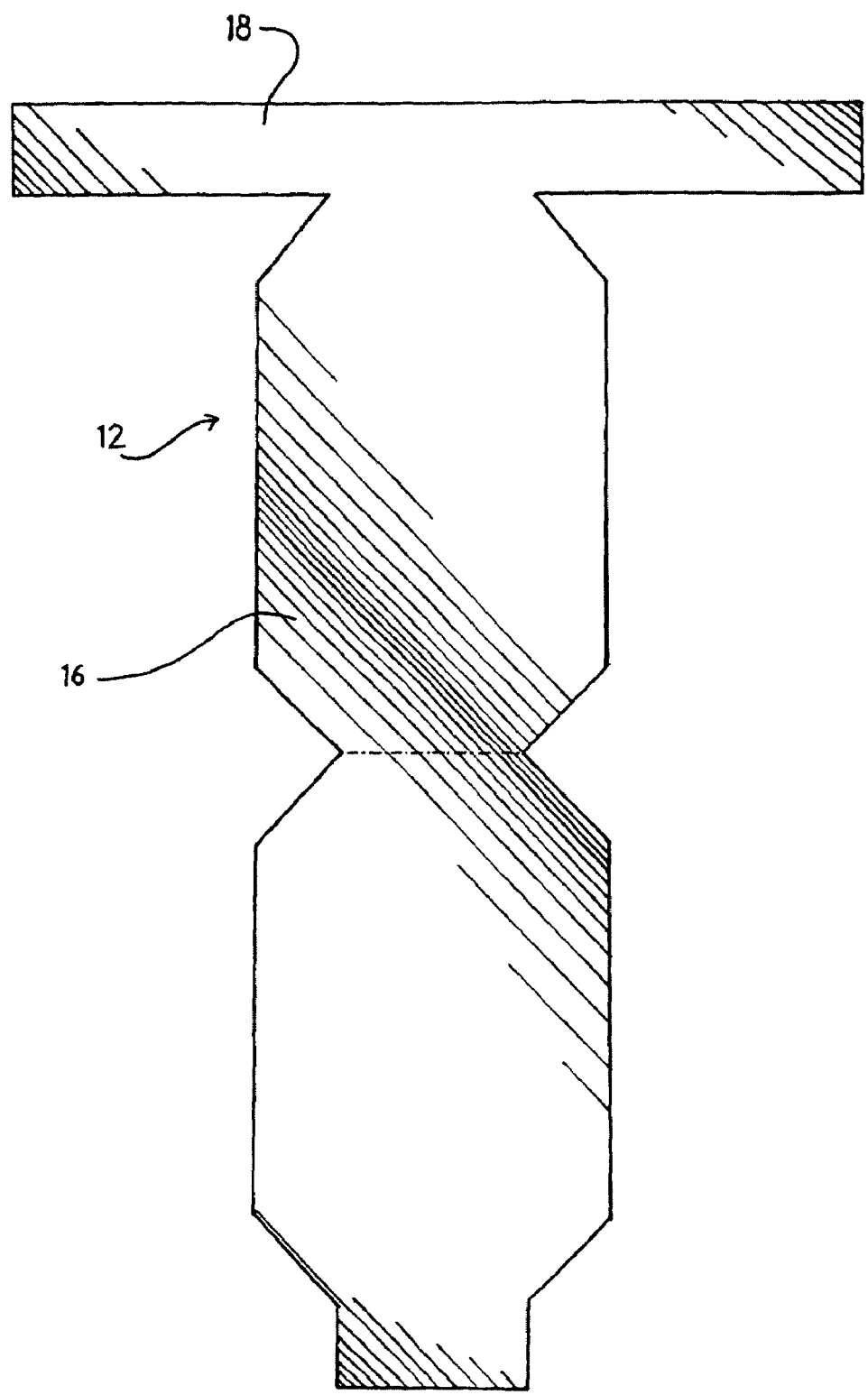
FIG. 3a is a plan view of one type of deformable element of the present invention.
Figure 3B:
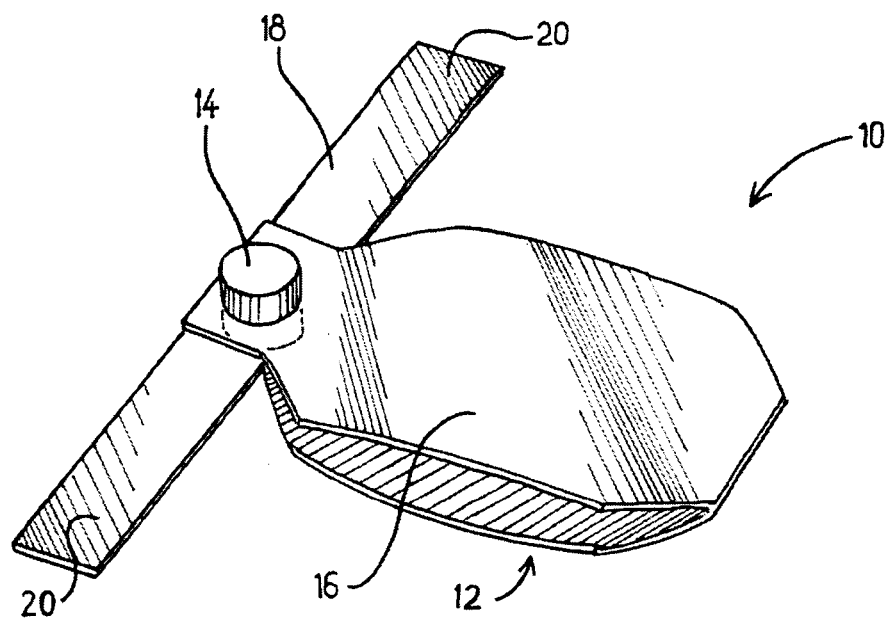

If flow-responsive element 12 is made from a single piece of material, steps can be taken to stiffen paddle portion 16 relative to torsion strip 18. For example, as shown in FIGS. 3a and 3b, paddle portion 16 can be made by folding the material at the dotted line, thereby making paddle portion 16 relatively stiff compared to torsion strip 18, and optimizing the twisting motion sensed by position sensors 14.

Although the embodiments described above utilize the change in position by deformation of a flexible material, such as Mylar®, other embodiments may use coil springs and the like to enable the flow responsive element to change position in response to fluid flow. Using a spring or similar device, rigid materials, such as glass or ceramics can be used to make the flow-responsive element. The sensitivity of such an embodiment will depend in part on the strength of the spring coil. Using such an embodiment provides a great deal of control over the range of sensitivity of the flow sensing apparatus.

Position sensor 14 can be any type of sensor capable of sensing a change in position or twisting of torsion strip portion 18 and generating a signal in response thereto. One preferred type of sensor is a Hall Effect Sensor (HES) with magnets positioned on opposite surfaces of torsion strip 18. When torsion strip 18 deforms, the magnets physically rotate together relative to their previous position. The rotation of the magnets results in the magnetic field rotating relative to the HES, thereby causing a change in the strength and/or the direction of the magnetic field through the active element of the HES. The change in the magnetic field causes a change in the output voltage of the HES, which is used to control the magnitude and direction of the gas flow through the positive air pressure device. Other position sensors, such as accelerometers or optical sensing devices, can also be used.

Figure 5:
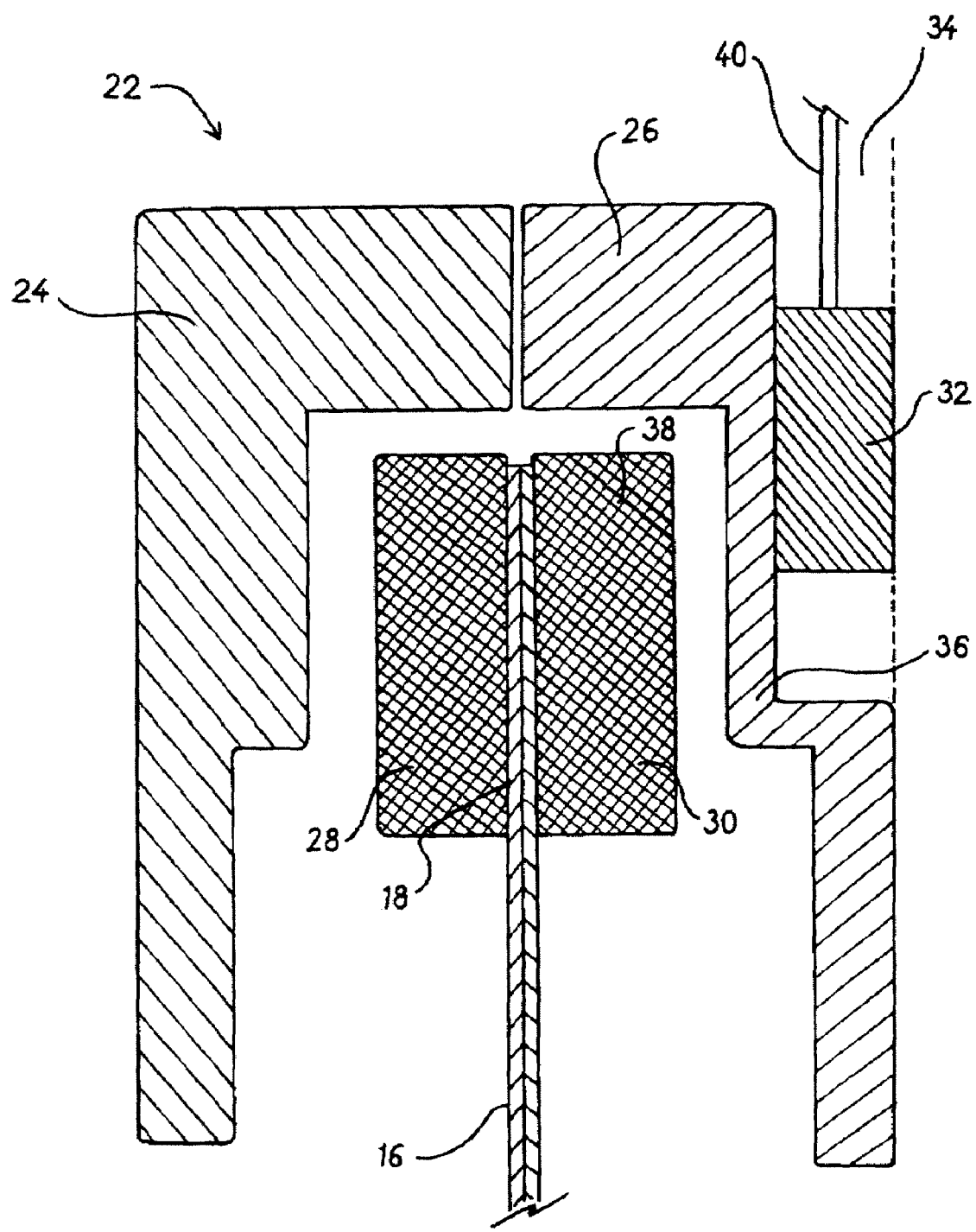
FIG. 5 is a side view of the flow sensor of the present invention shown in FIG. 4.

As best seen in FIG. 5, magnets 28 and 30 are preferably positioned opposite each other on either planar surface of torsion strip 18. Preferably, the magnets 28 and 30 of position sensor 14 are located at or near the center of torsion strip 18 to optimize sensitivity as shown in FIGS. 1 and 3b. However, the magnets 28 and 30 can be located anywhere along strip 18 other than at ends 20. The location of magnets 28 and 30 on torsion strip 18 will affect the sensitivity of the flow sensing apparatus.

Figure 4:
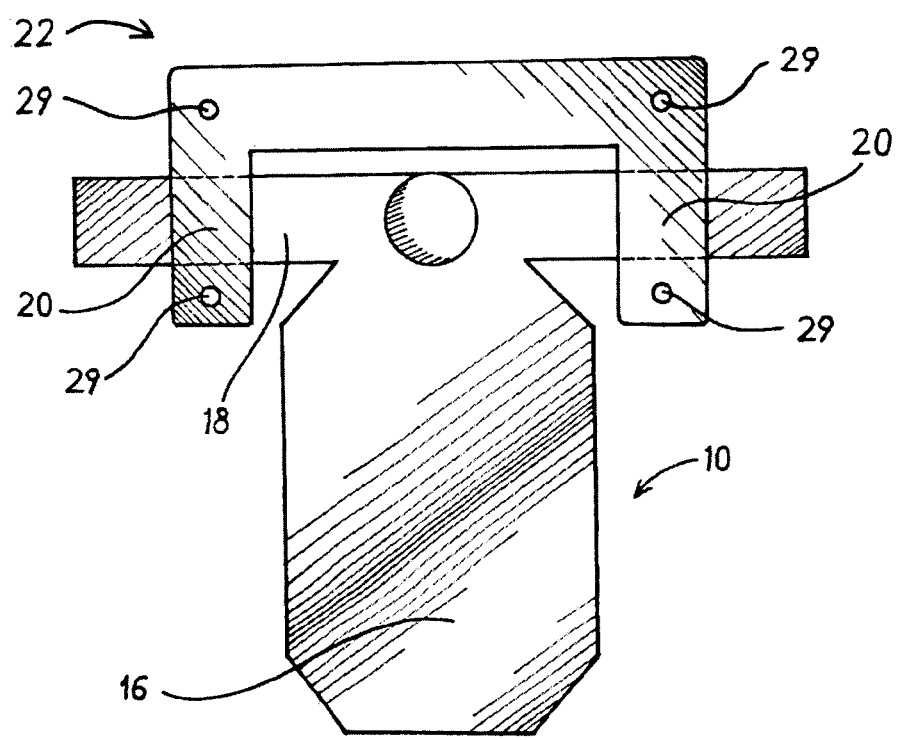
FIG. 4 is a plan view of one embodiment of the flow sensor of the present invention in a housing.

Ends 20 of torsion strip 18 can be fixed within a housing 22, as shown in FIG. 4. Ends 20 can be fixed by any method, such as adhesion, clamping, bolting, soldering, and the like, as long as the middle portion of torsion strip 18 between ends 20 is free to deform in response to a change in position of paddle portion 16. FIGS. 4 and 5 show housing 22 having clamping blocks 24 and 26 in between which ends 20 of torsion strip 18 are fixed. Clamping blocks 24 and 26 are held together by screws 29. Housing 22 should preferably also accommodate position sensor 14. In the embodiment shown in FIG. 5, clamping blocks 24 and 26 provide sufficient room for magnets 28 and 30 which are attached to torsion strip 18. Hall Effect Sensor 32 is positioned in a slot 34 in clamping block 26, and is preferably held in place with an adhesive or positive clamp or similar devices. FIG. 5 also shows wire 40 in communication with sensor 32, which can be connected to a fluid flow controller or other device (not shown) to control the fluid flow in response to the torque sensed by the magnets 28 and 30.

The tension in torsion strip 18 within housing 22 plays an important role in determining the overall sensitivity of flow sensor 10. To provide consistent tension in torsion strip 18, it is preferred to apply a measured amount of force to torsion strip 18 and hold torsion strip 18 at this initial tension while sensors 14 and housing 22 are attached to torsion strip 18. Housing 22 can then maintain the tension in torsion strip 18 when flow sensor 10 is used in a positive air pressure device. A change from the predetermined amount of initial tension in torsion strip 18 will then indicate the air flow rate within the PAP device.

Figure 6A:
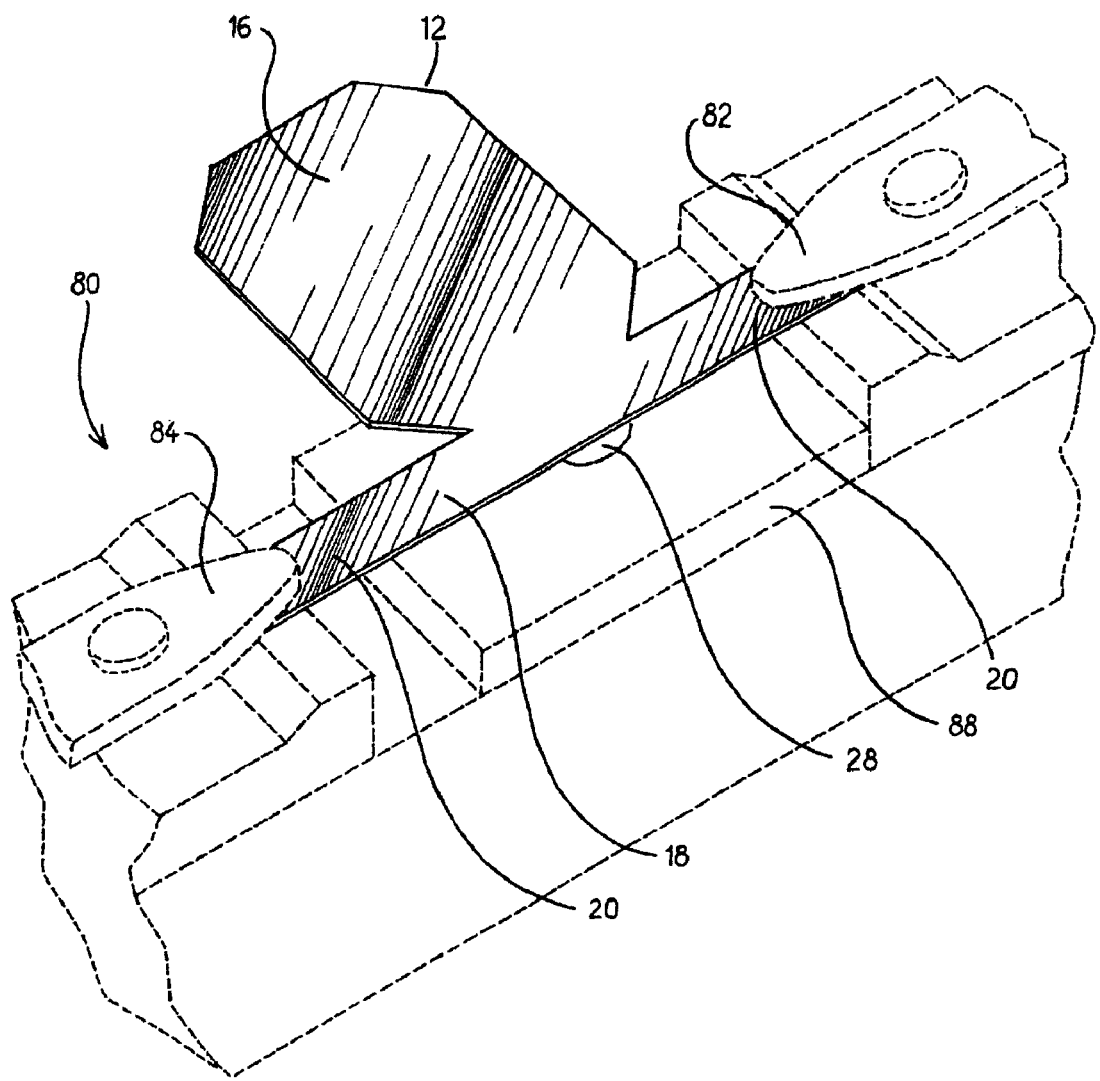
FIG. 6a shows one embodiment of an assembly jig for assembling the flow sensor of the present invention.
Figure 6B:
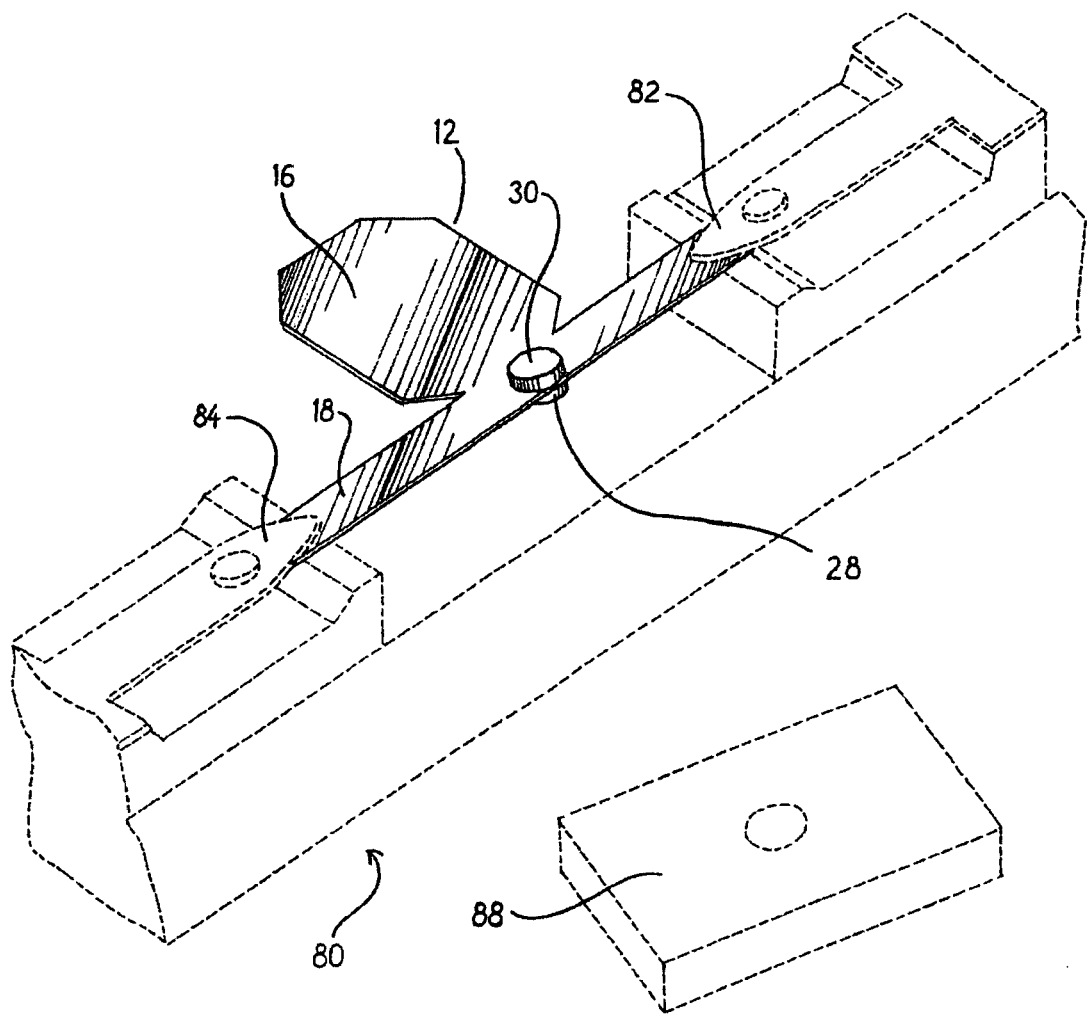
FIG. 6b shows the assembly jig of FIG. 6a with magnets attached to the deformable element of the present invention.
Figure 6C:
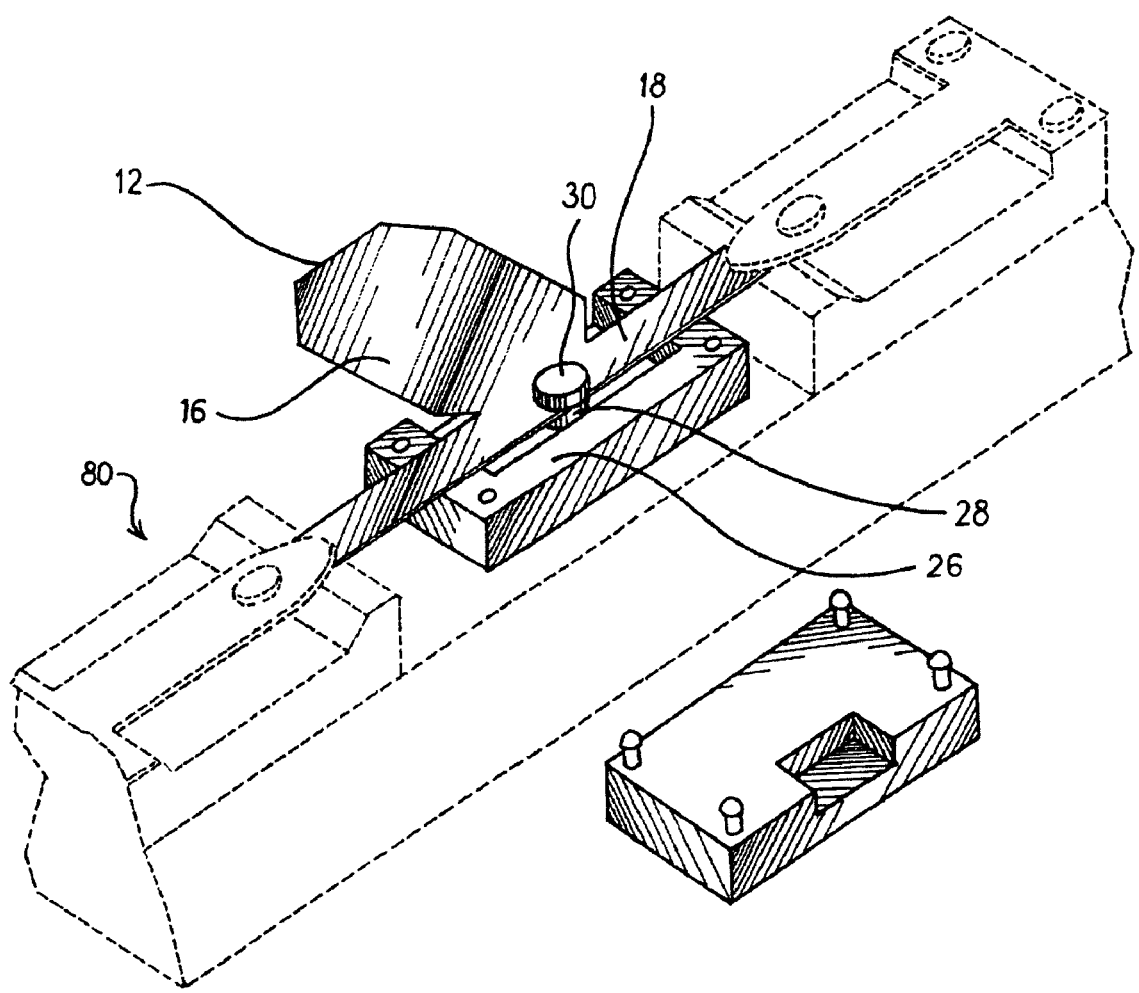
FIG. 6c shows the assembly jig of FIG. 6b with one part of the housing attached to the flow sensor of the present invention.

One method for applying tension forces to torsion strip 18 is shown in FIGS. 6a–c. The ends 20 of torsion strip 18 are clamped into assembly jig 80 in between clamps 82 and 84. Clamp 84 can be pulled axially by a calibrated spring balance 86 or similar device, thereby placing torsion strip 18 under a measured amount of tension force. In this position, sensors 14, such as magnets 28 and 30, can be placed on torsion strip 18 as shown in FIGS. 6a and 6b. In the embodiment shown, a magnet positioning block 88 is used to precisely align magnet 28 onto torsion strip 18. Other methods for positioning the magnets on the torsion strip can also be used.

FIG. 6c shows the positioning of clamping block 26 on one side of torsion strip 18. Clamping block 24 can be positioned on top of block 26 with torsion strip 18 positioned in between the two blocks. Once torsion strip 18 is secured between clamping blocks 24 and 26, the entire flow sensing unit, including clamping blocks 24 and 26, magnets 26 and 28, and flow responsive element 12 can be removed from the assembly jig simply by cutting the torsion strip 18 portions between the clamping blocks and clamps 82 and 84. The flow sensing unit can then be inserted into the desired location of a positive air pressure device.

In the embodiment shown in FIG. 6a, magnet 28 is offset from torsion strip 18. Magnet 30, seen in FIG. 6b, is similarly offset from strip 18. The magnets were offset in this embodiment to compensate for the weight of the paddle portion 16, which in this case was made by folding the Mylar® film having a thickness of 80 microns. By adjusting the magnet position to compensate for the weight of the paddle portion, the centers of gravity of the flow-responsive element and the position sensors in contact with the element are on axis, and therefore preferably do not twist or deform torsion strip 18 at the zero flow position. In the embodiment shown in FIG. 6a, the magnets are offset from the edge 90 of torsion strip 18 by about 2 mm. The skilled artisan will appreciate that the center of gravity of flow sensor 10 will depend on the materials used to make flow sensor 10, the relative size, shape and weight of paddle portion 16, and the size, weight and type of deformation sensors used.

In the embodiment shown in FIG. 6a, the effect of offsetting the magnets is to make the response of the Hall Effect Sensor more asymmetrical since the magnets now translate as well as rotate. The HES is preferably mounted on the upstream or blower side of the magnets to get the strongest response in the forward flow direction.

Using the method to assemble the flow sensor as shown in FIGS. 6a–c, the initial tension in torsion strip 18 can be set to any desired value. When using a Hall Effect Sensor, the initial torsion strip tension will determine the strength and clarity of the signal generated by the magnets. Torsion strip 18 is preferably held at an initial tension at which the effects of gravity on the HES output are reduced, and the effects of change in position such as mechanical deflection of paddle portion 16 are enhanced. Preferably, if Mylar® or other plastic or similar polymeric materials are used to make torsion strip 18, strip 18 is subjected to a minimum amount of initial tension so as to substantially reduce the creep rate of the polymeric material over time. In the embodiment shown in FIGS. 6a–c, the preferred tension was obtained by applying between about 250 grams to 1,000 grams force. More preferably, torsion strip 18 is under an initial tension of about 250 g force.

In addition to initial strip tension, the position of the HES relative to the magnets contributes to the strength and clarity of the signal generated and to the overall sensitivity of the flow sensing apparatus. The position of the HES relative to the magnets can be adjusted by monitoring the zero flow output of the HES. Preferably, the HES is positioned relative to the magnets such that the output voltage at zero flow is between about 1.5 V and 2.5 V, more preferably about 2.1 V, when the supply voltage is about 5.0 V, to attain the desired sensitivity. Wall 36, seen in FIG. 5, between the HES 32 and magnet 30 is as thin as possible, preferably about 0.5 mm. In the embodiment shown in FIG. 5, the center of HES 32 is positioned approximately aligned with the edge 38 of magnet 30 to optimize sensitivity.

Housing 22 can be made of any rigid materials that does not substantially interfere with the operation of the flow sensor 10. Preferably, housing 22 is machined from a material such as acetal, acrylic, polyvinylchloride (PVC) or other similar materials.

HES 32 can be any commercially available sensor. Magnets 28 and 30 can be any type of magnet useful with HES 32. Preferably, rare earth button magnets that are strong enough to hold themselves onto torsion strip 18 are used. In one preferred embodiment, nickel-plated neodymium button magnets having a diameter of 6 mm and a height of 2 mm are used. One preferred embodiment of the flow sensing apparatus of the present invention has a sensitivity, defined as the slope of the output voltage versus flow characteristic, that is inversely related to the fluid dynamic pressure, defined as the dynamic pressure in the channel when paddle portion 16 is not present, at gas flow rates greater than about 20 l/min. In other words, the apparatus of the present invention has a higher sensitivity at low pressures, and a lower sensitivity at high pressures. In this embodiment, low pressure is defined as the fluid flow pressure generated by a gas flow rate of between about 20 l/min to 60 l/min, and high pressure is defined as the fluid flow pressure generated by a gas flow rate greater than about 60 l/min.

The sensitivity of this direct-measurement flow sensing apparatus contrasts with the characteristics of the more common pressure-differential-producing sensors (e.g. orifice or venturi) in which the sensitivity reduces as the flow rate reduces. In pressure differential sensors, the fluid dynamic pressure is measured at two points, one upstream and one downstream from a restriction in the cross-sectional area through which the fluid is flowing. The pressure differential between these two points can be used to determine fluid flow rates based on a calibration plot, correlating known flow rates with a corresponding pressure differential. At very low flow rates, the pressure differential becomes very low, and, as a result, the sensitivity of the sensor also necessarily decreases. To obtain sufficient signal-to-noise ratio at low flows in such sensors, a very expensive pressure transducer is required.

Figure 13:
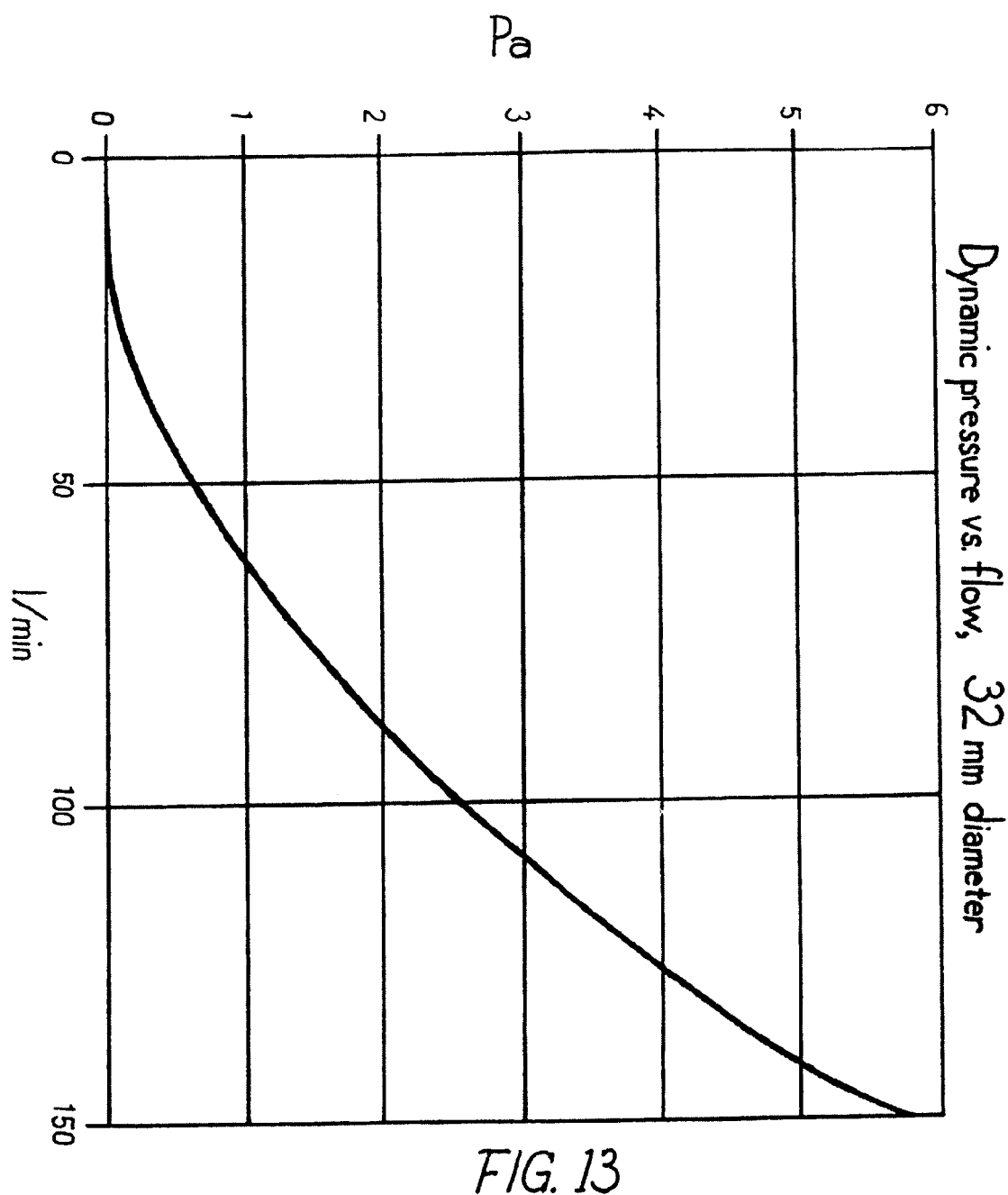
FIG. 13 is a plot of dynamic pressure versus flow rate of a positive air pressure system.

In positive air pressure systems, the ability to measure the lower flow rates accurately is a significant advantage since many sleep-related disorders involve momentary lapses of breathing or irregular breathing patterns during which the fluid dynamic pressure is quite low. Those skilled in the art will appreciate that the fluid dynamic pressure varies not only with flow rate, but with the diameter of the orifice through which the fluid is flowing. Because of the wide range of pressures a positive air pressure device must accommodate, the gas flow duct or hose typically has a diameter that necessarily results in very low fluid dynamic pressure at low flow rates as seen, for example, in FIG. 13. It is precisely at these low flow rates and corresponding low fluid dynamic pressures that the flow sensing apparatus of the present invention demonstrates the most sensitivity. In addition, the reduced sensitivity at higher fluid flow rates is advantageous in positive air pressure systems because the increased sensitivity at higher flow rates of other flow sensors is not useful and only unnecessarily uses up the dynamic range of the output voltage.

Unlike the flow switches commonly used to detect breathing direction in respiratory devices, which can only indicate breathing "in" or "out", the flow sensor of the present invention provides output information along a continuum indicating whether the patient is inhaling or exhaling and the depth or strength of the patient's respiration.

In most positive air pressure systems, there is a continuous positive air flow to the patient, even when the patient exhales. There is usually provided some leakage flow mechanism, such as through the patient mask, to vent out the excess air. The air flow through the air duct of the PAP does not change direction during the breathing cycle because the leakage flow generally exceeds the exhalation flow.

In some cases, if the leakage flow rate is less than the exhalation flow the direction of air flow may, momentarily, reverse. If the direction of the air flow changes for too long, the patient may rebreathe exhaled air. Since the flow sensing apparatus of the present invention is highly sensitive at low fluid dynamic pressures and can detect a reverse or negative fluid flow, it can be used to monitor whether rebreathing or other dangerous conditions may be occurring. The flow sensing apparatus can be used as an early warning system for detecting insufficient positive fluid pressure, indicating some sort of problem with the patient's breathing.

It is desired to provide a positive air flow to the patient at different pressures depending on the patient's breathing cycle. The sensitivity of the patient breath flow sensing apparatus, therefore, determines how well the PAP system responds to the patient.

The flow sensing apparatus of the present invention is highly sensitive to very low fluid flow rates. Preferably, the flow sensing apparatus can measure gas flow rates ranging from about −10 l/min. to about 150 l/min. The negative flow rate values are an indication of patient rebreathing. Upon detecting rebreathing, the flow sensing apparatus sends an appropriate signal to the PAP device so that the problem can be corrected.

Figure 7:
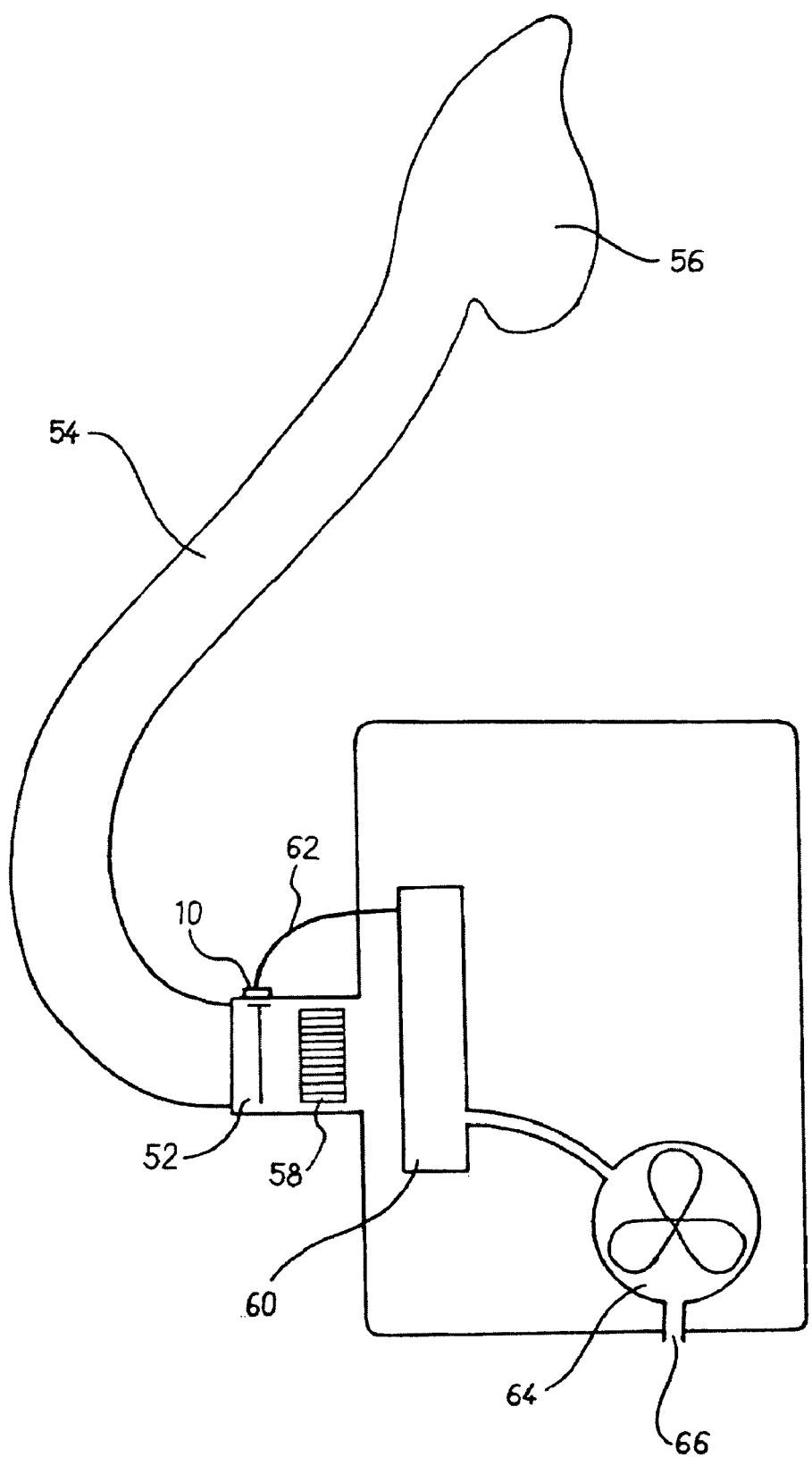
FIG. 7 is a schematic diagram of the flow sensor of the present invention used in a positive air pressure system.

FIG. 7 shows flow sensor apparatus 10 in operation in conjunction with positive air pressure device 50. PAP device 50 includes air flow controller 60, and may also include, inter alia, a blower 64 and a processor (not shown). PAP device 50 includes an air duct 52, into which flow sensing apparatus 10 can be positioned. Duct 52 is connected to hose 54, which is connected to breathing interface 56. Breathing interface 56 can be any type of patient breathing interface, such as a mask fitting over the patient's nose and mouth. Apparatus 10 senses the patient's breathing and sends a corresponding signal to the controller via connector 62. The controller 60, in turn, controls the air pressure delivered to the patient. Controller 60 is in fluid communication with blower 64. Blower 64 includes intake 66 in fluid communication with the atmosphere.

Although sensor 10 is shown in FIG. 7 as being positioned in air duct 52, sensor 10 can be positioned anywhere along the air delivery path including intake 66, duct 52, hose 54, and interface 56.

Figure 8:
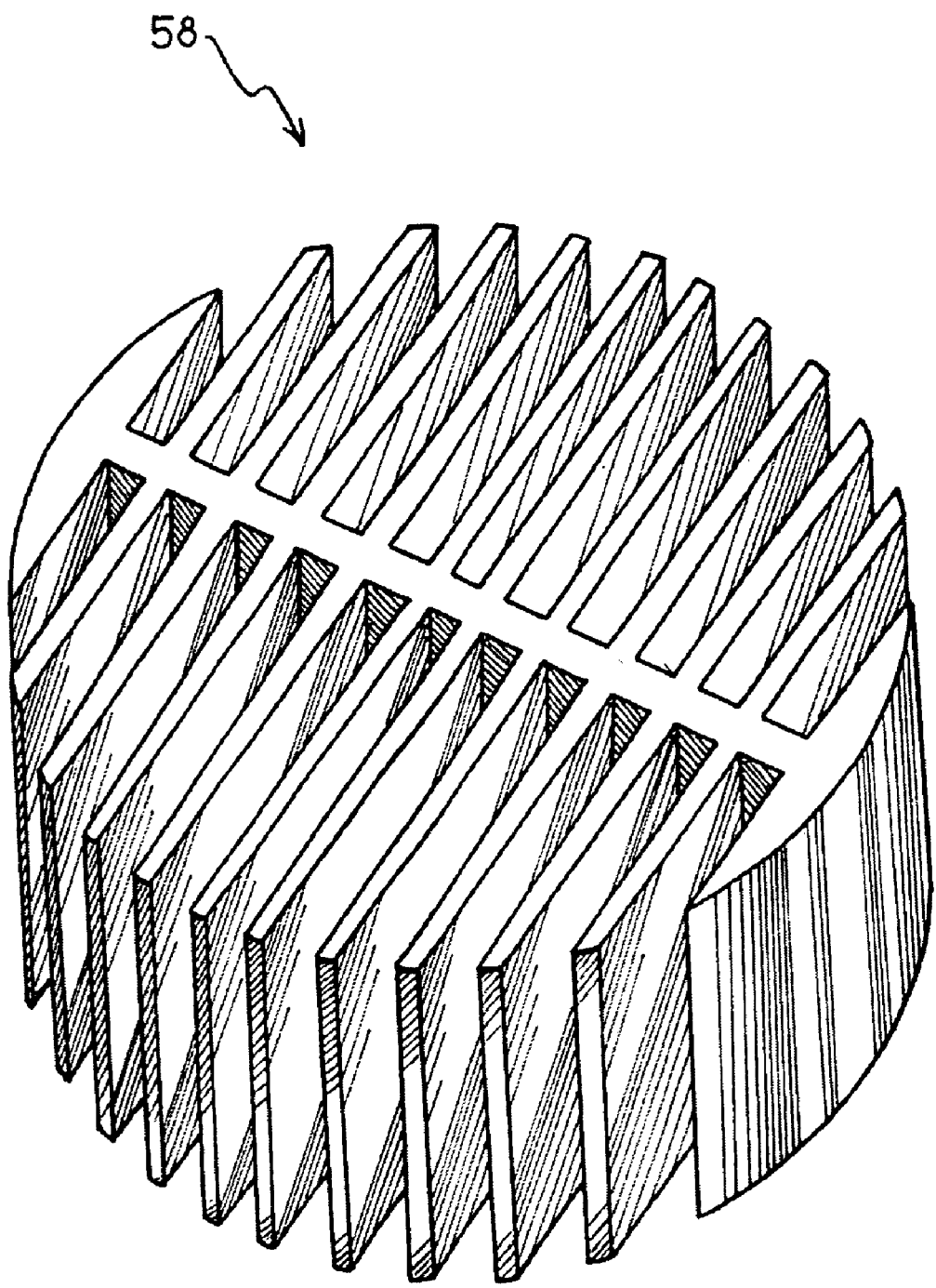
FIG. 8 is a perspective view of one embodiment of a flow corrector of the present invention.

In a preferred embodiment, a flow corrector or straightener is used in conjunction with flow sensor 10 to further enhance the sensitivity of sensor 10 to a patient's breathing. The flow corrector serves to reduce air turbulence coming from the blower, so that the sensor can more accurately detect changes in the patient's breathing. As shown in FIG. 7, flow corrector 58 can be positioned upstream of flow sensor 10 in air duct 52. FIG. 8 shows one example of flow corrector 58. Preferably flow corrector 58 is positioned as close as possible to flow sensor 10 without interfering with the sensor's operation. In one preferred embodiment, flow corrector 58 is positioned about 6 mm upstream from sensor 10.

As seen in the figures, paddle portion 16 of flow-responsive element 12 projects into the fluid flow path approximately perpendicular to the flow direction to optimize sensitivity of element 12. The size of paddle portion 16 will vary depending on the cross-sectional area of the fluid flow path. As the size of the paddle 16 approaches the dimension of the cross-sectional area of the fluid flow path, fluid dynamic pressure is applied to a greater surface area of the paddle, increasing the torque applied to torsion strip 18 and enhancing the overall sensitivity of the sensing apparatus. At the same time, the larger the size of the paddle, the greater the restriction to the flow passing through the sensor, which may adversely affect the sensitivity of the flow sensing apparatus. Therefore, the size of the paddle portion should be selected to optimize the sensitivity of the sensing device while minimizing the possible restriction to the fluid flow.

If the paddle is too small, it will respond to turbulence associated with the boundary layer and the housing. It is therefore preferred that the paddle project into the free stream portion of the fluid flow. Generally, it is preferred that the paddle project into the flow by greater than 10% of the flow path diameter. The paddle projection into the flow path can approach 100% of the flow path diameter. However, the paddle must be clear of the duct walls to remain functional at all operational flow rates.

The shape of the paddle can be similarly selected to optimize sensitivity while minimizing the effects of drag forces and other factors affecting the signal-to-noise ratio. The selection of a suitable shape is a function of the flow range being monitored and the signal-to-noise ratio. Preferably, a wide, elongate paddle, as shown in FIG. 1, is used as it generates a significant amount of torque while providing a desired sensitivity level. Other shapes may be suitable depending on the size and shape of the duct and the degree of sensitivity desired.

The flow-responsive element of the flow sensing device may also be sensitive to gravitational forces. If the apparatus is rotated from its normal use position, the deformable element may lose some sensitivity. This effect can be counteracted by using sensors, such as magnets, of a selected weight, selectively positioned on the torsion strip portion to reduce the effects of gravity on the overall sensitivity of the device.

EXAMPLE 1

Figure 9:
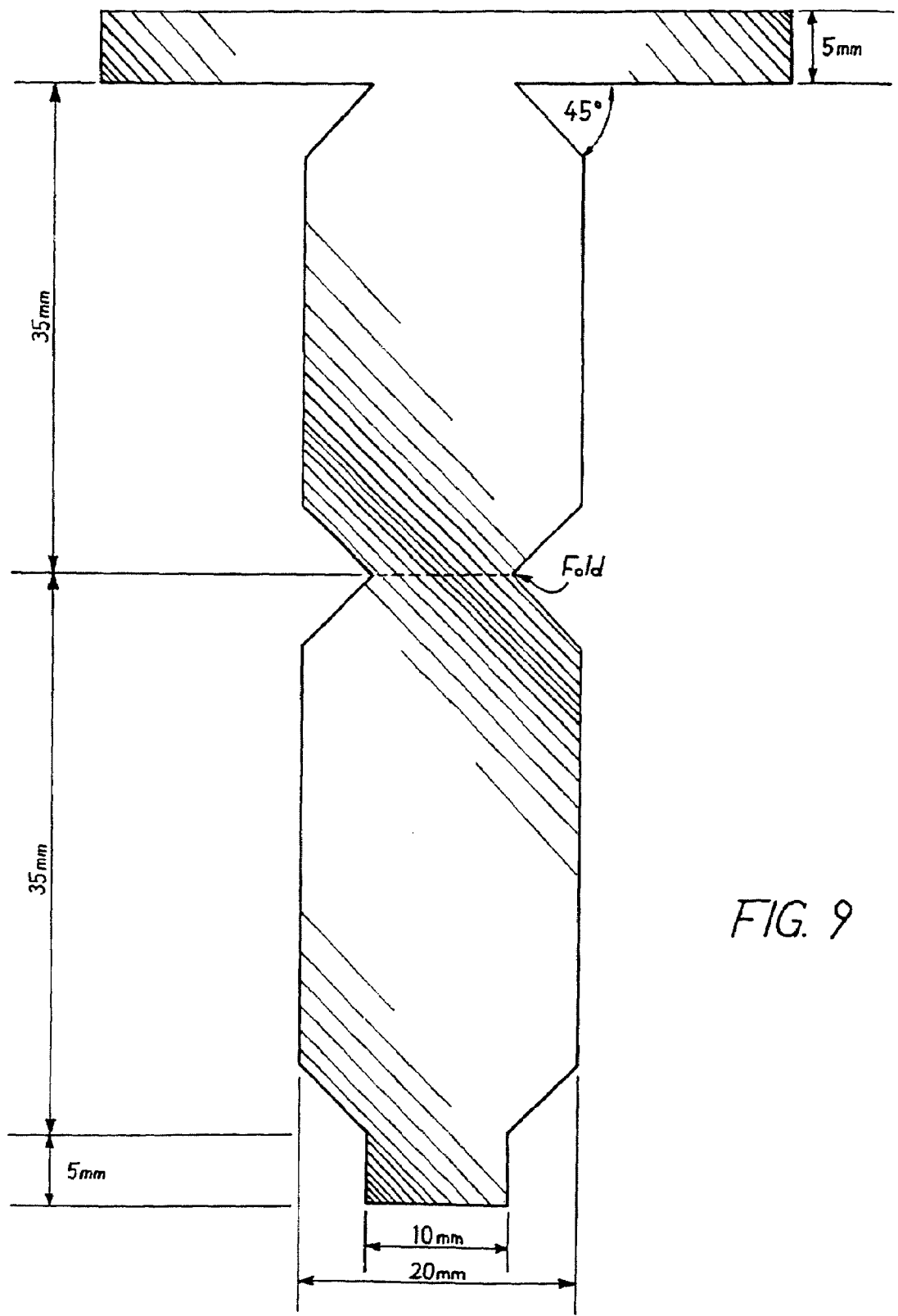
FIG. 9 is a plan view of one embodiment of the deformable element of the present invention with dimensions.

To demonstrate the inverse relationship between flow sensor sensitivity and flow rate, the output voltage was measured over a range of flow rates. An 1,800 mm long hose having a diameter of 20 mm was attached to a centrifugal blower by a duct to generate air flow through the hose. The duct had a diameter of 32 mm at the blower outlet end and tapered down to a diameter of about 20 mm at the hose attachment end. The blower included a motor which could drive the rotor to 12,000 RPM. A flow sensor made of Mylar® having a thickness of 80 microns, with a paddle portion having the shape and dimensions shown in FIG. 9, was attached within the duct adjacent to the blower outlet.

Figure 10:
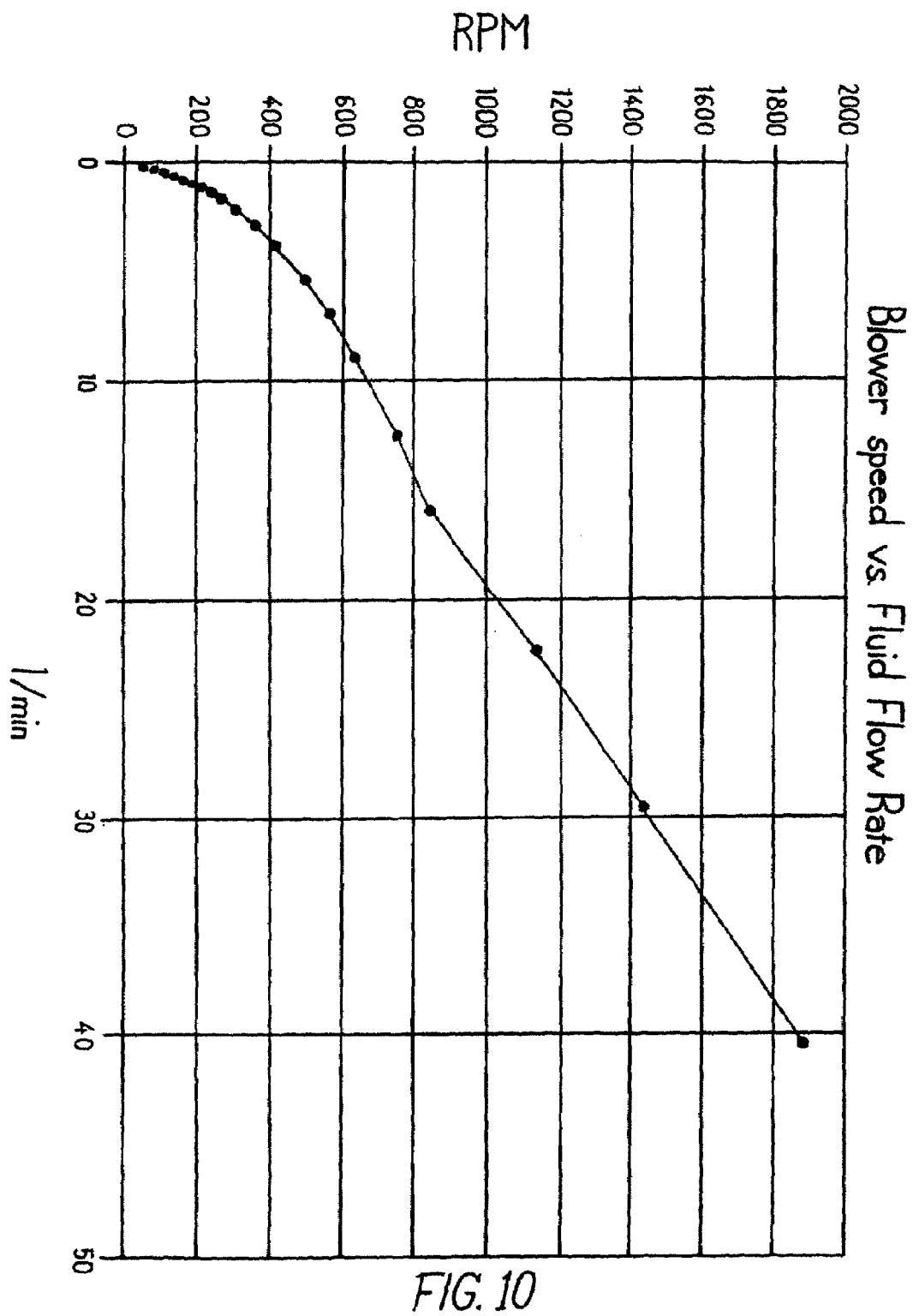
FIG. 10 is the calibration plot used to calibrate the blower in Example 1.

The blower and hose assembly was calibrated based on speed versus output flow. As seen in FIG. 10, the relationship between blower speed and flow rate is linear except at very low blower speeds, where laminar conditions have a greater impact on the flow rate. From the data shown in FIG. 10, the following equations were derived to translate measured blower RPM to flow rate:

$$\text{For RPM} > 900, \text{flow rate}(1/\min) = \frac{\text{RPM} - 273}{39}$$

$$\text{For RPM} < 900, \text{flow rate}(1/\min) = (\text{RPM}/212.6)^2$$

Figure 11:
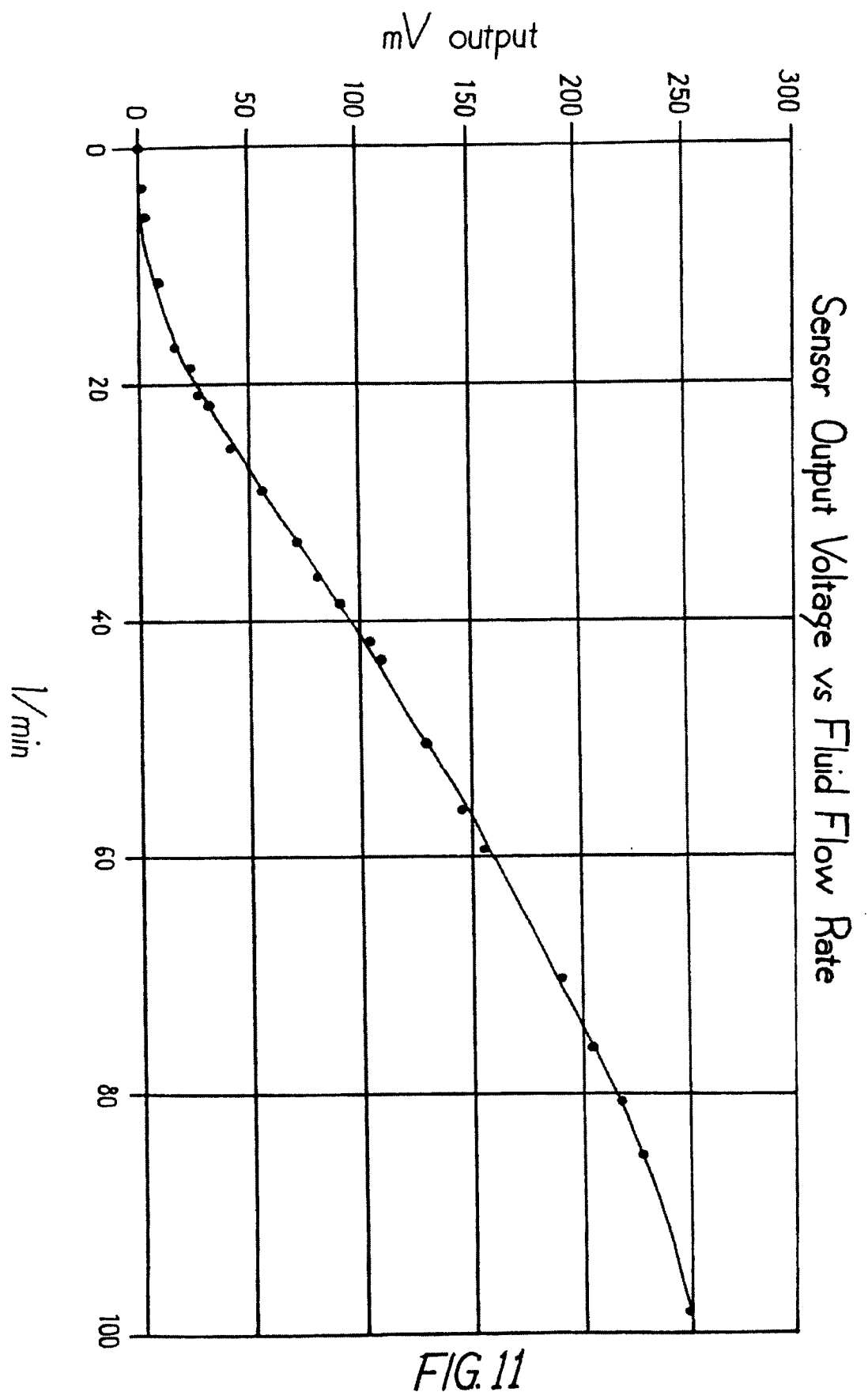
FIG. 11 is a plot of output voltage vs. flow rate using the flow sensor of the present invention.

The flow sensor was then tested by recording the HES output voltage deviation from the zero-flow rate against the blower RPM (converted to flow rate using the equations described above). The results are shown in FIG. 11. As can be seen, the sensor has a higher sensitivity (seen as a greater slope of the output voltage plot) at low flow rates (20 l/min to 60 l/min) and a lower sensitivity at higher flow rates (greater than 60 l/min). The highest sensitivity of this example is at about 30 l/min, which corresponds to the preset exhaust flow of a typical positive air pressure device mask. This coincides with zero patient flow, making the sensor particularly useful for detecting the beginning of inhalation or exhalation.

Since a typical PAP device primarily operates at between 30 l/min and 150 l/min, the increased sensitivity at lower flow rates of the sensor of the present invention is a significant improvement over previous methods or devices, as further exemplified below.

EXAMPLE 2

Figure 12:
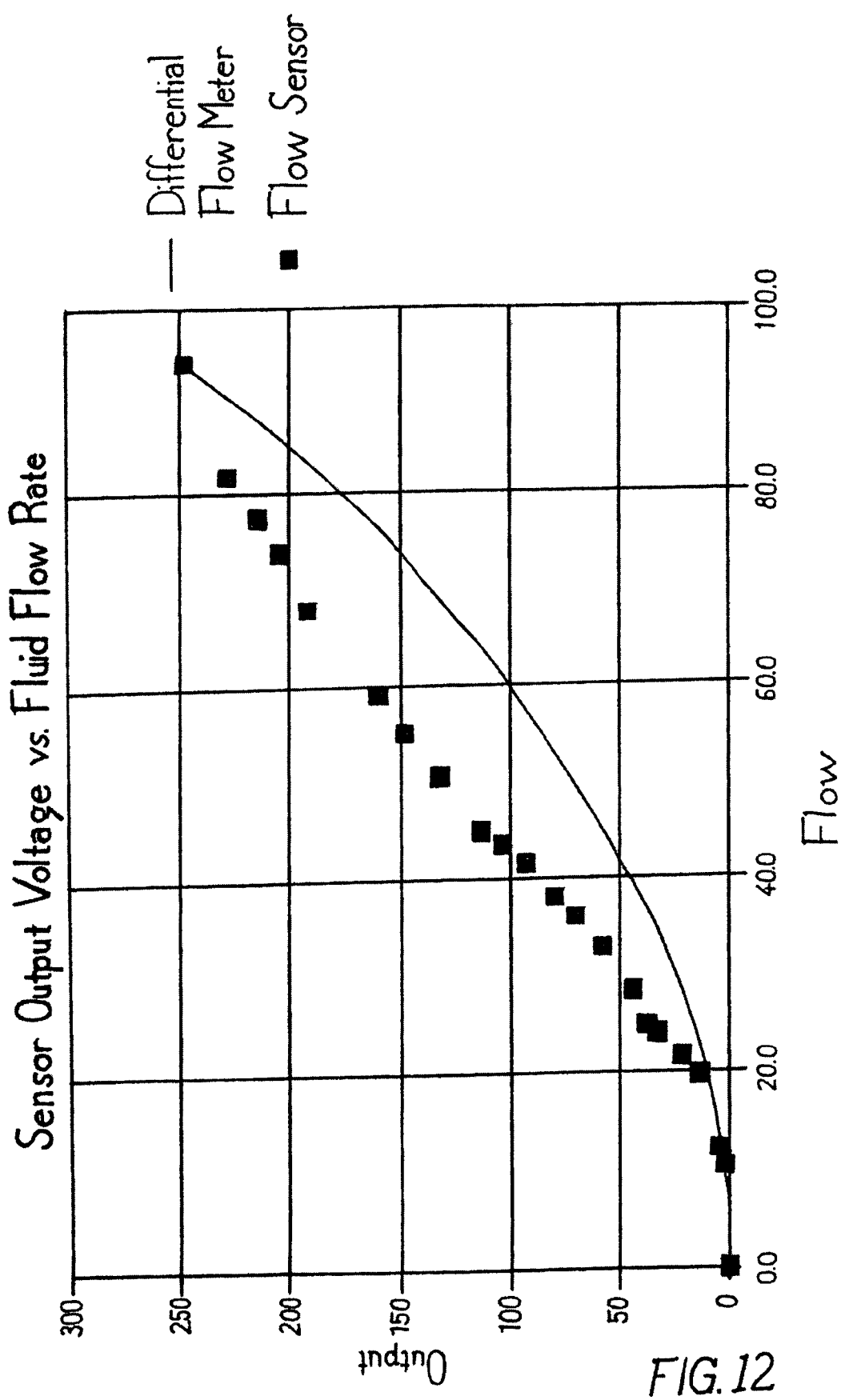
FIG. 12 is a comparative plot of output voltage versus flow rate of the flow sensor of the present invention and a differential flow meter.

The sensitivity of the flow sensor of the present invention was compared to the sensitivity of a conventional pressure-differential flow meter. The results are shown in FIG. 12. By comparing the slopes of the output voltage characteristics, it can be seen that at lower flow rates the sensitivity or slope of the output voltage of the flow sensor of the present invention is higher than at high flow rates. In contrast, the sensitivity of the pressure differential flow meter gradually increases with increasing flow rate, and is less sensitive than the flow sensor of the present invention at low flow rates.

Although the description and figures describe some embodiments of the present invention, many other embodiments and variations of the flow sensing apparatus are encompassed by the teachings of the present invention. It is therefore understood that the foregoing text and figures are not intended to limit the scope of the present invention, which is fully set forth in the claims recited hereinbelow.

What is claimed is:

1. A fluid flow sensing apparatus comprising:
   a flow-responsive element projecting into a fluid flow path, the flow-responsive element including a paddle section and a torsion strip section
   a magnet coupled to the flow-responsive element and adapted to be displaced in response to the torque level generated by the flow-responsive element; and
   a sensor for detecting a change in position of the magnet.

2. The flow sensing apparatus of claim 1, wherein the apparatus has a sensitivity that is generally inversely related to a pressure generated by the fluid flow.

3. A flow sensing apparatus comprising:
   a mask portion;
   a hose, the hose cooperating with the mask portion to define an air pathway;
   a deformable element projecting into the air pathway;
   a magnet coupled to the deformable element; and
   a sensor adapted to detect a position change of the magnet.

4. The apparatus of claim 3, wherein the sensor includes a Hall effect sensor.

5. A flow sensing apparatus comprising:
   a mask portion;
   a hose, the hose cooperating with the mask portion to define an air pathway;
   a deformable element projecting into the air pathway, wherein the deformable element includes a paddle section and a torsion strip;
   a magnet coupled to the deformable element; and
   a sensor adapted to detect a position change of the magnet.

6. A flow sensing apparatus comprising:
   a fluid pathway;
   a deformable element projecting into the fluid pathway, the deformable element including a paddle section and a torsion strip section;
   a magnet coupled to the torsion strip section; and
   a sensor adapted to detect movement of the magnet.

7. The apparatus of claim 6 wherein the sensor includes a Hall effect sensor.

8. The apparatus of claim 6 wherein the sensor is adapted to communicate with a gas delivery device.

* * * * *